United States Patent [19]

Rosini et al.

[11] Patent Number: 5,451,606
[45] Date of Patent: Sep. 19, 1995

[54] ANTHRAQUINONE COMPOUNDS USEFUL TO TREAT OSTEOARTICULAR CONDITIONS, PHARMACEUTICAL COMPOSITIONS AND METHOD OF TREATMENT

[75] Inventors: Sergio Rosini; Maurizio Mian, both of Pisa, Italy

[73] Assignee: Istituto Gentili S.p.A., Pisa, Italy

[21] Appl. No.: 117,065

[22] PCT Filed: Mar. 4, 1992

[86] PCT No.: PCT/EP92/00479
§ 371 Date: Oct. 6, 1993
§ 102(e) Date: Oct. 6, 1993

[87] PCT Pub. No.: WO92/16496
PCT Pub. Date: Oct. 1, 1992

[30] Foreign Application Priority Data

Mar. 12, 1991 [IT] Italy ................... MI91A0658

[51] Int. Cl.[6] ............. C07C 235/66; A61K 31/195
[52] U.S. Cl. ......................... 514/563; 552/262
[58] Field of Search ....................... 552/262; 514/563

[56] References Cited

U.S. PATENT DOCUMENTS 4,966,918 10/1990 Watanabe et al. ............... 552/262

FOREIGN PATENT DOCUMENTS 2508798 1/1983 France .

Primary Examiner—Rebecca Cook
Attorney, Agent, or Firm—Bucknam and Archer

[57] ABSTRACT

The present invention concerns a compound of formula (I)

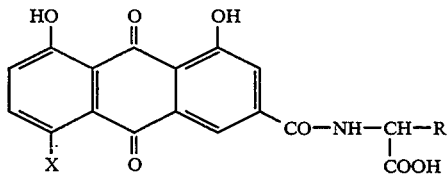

wherein:
X is selected from H and OH;
R is a residue which, linked to the

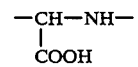

group, forms an amino acid; the enantiomers and racemic mixtures thereof; and the pharmaceutically acceptable salts thereof.

The invention further concerns a pharmaceutical composition which comprises the above compound or salts thereof and the use of the compound for treating an articular pathology.

5 Claims, No Drawings

ANTHRAQUINONE COMPOUNDS USEFUL TO TREAT OSTEOARTICULAR CONDITIONS, PHARMACEUTICAL COMPOSITIONS AND METHOD OF TREATMENT

This application is a 371 of PCT/EP 92/00479 filed Mar. 4, 1992.

The present invention relates to compounds of general formula (I)

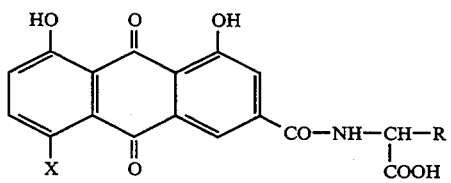

wherein:
X is selected from H and OH;
R is a residue which, linked to the

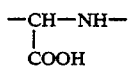

group, forms an amino acid; the enantiomers and racemic mixtures thereof; and the pharmaceutically acceptable salts thereof. Particularly preferred are those compounds in which R is a residue which, linked to the

group, forms a natural amino acid.

The compounds of the invention derive from rhein, which has some therapeutic properties; particularly known is the antiarthritic activity of diacerhein, which is the rhein diacetyl derivative.

The derivatives of rhein with natural amino acids, which are the object of the present invention, proved to have interesting pharmacological activities which make them useful for the treatment of articular pathologies. In fact, preliminary pharmacological research evidenced a marked inhibiting action on the elastase activity of human leukocytes, as well as an inhibiting activity on free radical formation.

The compounds of the invention are prepared according to conventional methods. Condensation of diacetylrhein with a compound of formula

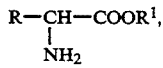

wherein $R^1$ is a $C_1$–$C_4$ alkyl group, is carried out in anhydrous solvents such as methylene chloride, and in the presence of acid-binding agents, for example triethylamine. The 4,5-hydroxy groups, and optionally the 8-hydroxy group, on the aromatic ring, and the carboxy group on the amino acidic portion are restored by means of hydrolysis of the corresponding esters. An embodiment of the invention comprises the use of diacetylrhein chloride.

The following examples further illustrate the invention.

EXAMPLE

2-[[4,5-Dihydroxy-9,10-dihydro-9,10-dioxo-2-anthracene-yl]carbonyl]amino-4-methyl-pentanoic acid.

3.1 g (8 mmoles) of 4,5-dihydroxy-9,10-dihydro-9,10-dioxo-2-anthracenecarboxylic acid chloride are added under stirring to a solution of dichloromethane (70 ml) containing 1.8 g (10 mmoles) of methyl 2-amino-4-methyl-pentanoate hydrochloride, 50 mg of p-N,N-dimethylamino-pyridine and 2.4 ml (16 mmoles) of triethylamine. The mixture is refluxed for 5 minutes, then it is left under stirring at room temperature for a night.

The reaction is controlled by means of thin layer chromatography on silica gel plates, using as eluent dichloromethane-diethyl ether in a 10:1 ratio.

At the end of reaction, the reaction mixture is washed with water, the organic phase is separated and solvent is evaporated off under reduced pressure and the residue is taken up into 50 ml of methanol and a solution of 5 g of potassium hydroxide in 50 ml of water, to obtain a purple solution. After about 30 minutes, the solution is acidified with 8% hydrochloric acid and filtered.

The precipitate is crystallized from an acetone-diethyl ether mixture, to obtain about 1,4 g of a product with
m.p.=204°–206° C.

| Elementary analysis for $C_{21}H_{19}NO_7$ | | |
|---|---|---|
| | calculated % | found % |
| C | 63.47 | 63.40 |
| H | 4.81 | 4.77 |
| N | 3.52 | 3.56 |

I.R. in agreement
$^1$H N.M.R. in agreement.

Analogously, the following compounds were prepared:

| Ex. N | R | Formula | M.p. |
|---|---|---|---|
| 2 | $(CH_3)_2CH-$ | $C_{20}H_{17}NO_7$ | >210° C. |
| 3 | $CH_3S(CH_2)_2-$ | $C_{20}H_{17}NO_7S$ | |

The elementary analysis and the IR and $^1$H-NMR spectra are in agreement with the formulae and structures.

The compounds of the invention, due to the above mentioned pharmacological properties thereof, can be used as active ingredients in pharmaceutical forms prepared according to known techniques.

Examples of pharmaceutical forms are tablets, capsules, powders, syrups, injectable forms, suppositories.

The dosage unit will range from 5 to 500 mg of active ingredient per dose. The posology will depend on the severity of the disease to treat and the patient's conditions.

We claim:
1. A compound of formula (I)

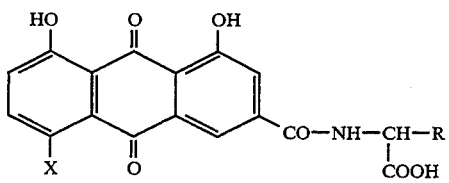

wherein:

X is H or OH;

R is isopropyl, isobutyl or methylthioethyl the enantiomer, the racemic mixture thereof, or a pharmaceutically acceptable salt thereof.

2. The compound according to claim 1, wherein in said formula(I) the group

—NH—CH—R
  |
  COOH forms a natural aminoacid.

3. A pharmaceutical composition containing 5–500 mgs per unit dose of a compound according to claim 1 as the active ingredient in admixture with pharmaceutically acceptable carriers and excipients.

4. The composition according to claim 3, in the form of a tablet, a capsule, a powder, a syrup or a suppository.

5. A method of treating an articular pathology in a patient affected thereby which consists of administering to said patient an effective amount of a compound according to claim 1.

* * * * *